United States Patent [19]

Behr et al.

[11] Patent Number: 5,476,962
[45] Date of Patent: Dec. 19, 1995

[54] NEW LIPOPOLYAMINES, THEIR PREPARATION AND THEIR USE

[75] Inventors: Jean-Paul Behr; Jean-Philippe Loeffler, both of Strasbourg, France

[73] Assignee: Centre National de la Recherche Scientifique, Paris, France

[21] Appl. No.: 191,068

[22] Filed: Feb. 3, 1994

Related U.S. Application Data

[63] Continuation of Ser. No. 922,887, Jul. 31, 1992, abandoned, which is a continuation of Ser. No. 509,788, Apr. 17, 1990, Pat. No. 5,171,678.

[30] Foreign Application Priority Data

Apr. 17, 1989 [FR] France .................................. 89 05037

[51] Int. Cl.$^6$ .................................................. C07C 229/00
[52] U.S. Cl. .................................................. 560/168
[58] Field of Search .............................................. 560/158

[56] References Cited

U.S. PATENT DOCUMENTS 5,171,678  12/1992  Behr et al. ............................ 435/172.3

OTHER PUBLICATIONS

Boeckman, Jr. et al, Journal of Organic Chemistry, vol. 51, #26, pp. 5486–5489, 1986.
Tetrahedron Letters, vol. 27, No. 48, 1986, pp. 5861–5864, Pergamon Journals Ltd., J. P. Behr, "DNA Strongly Binds to Micelles and Visicles Containing Lipopolyamines or Lipointercalants".

Proceedings of National Academy of Sciences of USA, vol. 86, No. 18 Sep. 1989, pp. 6982–6986 J. P. Behr, et al. "Efficient Gene Transfer into Mammalian Primary Endocrine Cells with Lipopolyamine–coated DNA".

*Primary Examiner*—José G. Dees
*Assistant Examiner*—Deborah D. Carr
*Attorney, Agent, or Firm*—Finnegan, Henderson, Farabow, Garrett & Dunner

[57] ABSTRACT

Intermediate compounds useful for producing transfecting lipopolyamines, comprising:

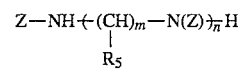

wherein m is an integer between 2 and 6 inclusive, wherein n is an integer between 2 and 5 inclusive, wherein $R_5$ represents a hydrogen atom or a carboxyl radical but no more than one $R_5$ represents a carboxyl, the values of m in the different fragments $(CH)_m$ may be identical or different, and wherein the symbol Z $R_5$ represent a group protecting the amine function.

5 Claims, No Drawings

NEW LIPOPOLYAMINES, THEIR PREPARATION AND THEIR USE

This is a continuation of application Ser. No. 07/922,887, filed on Jul. 31, 1992, now abandoned which is a continuation of application Ser. No. 07/509,788, filed on Apr. 17, 1990, now U.S. Pat. No. 5,171,678.

The present invention relates to new lipopolyamines of general formula:

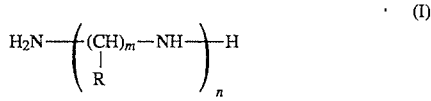

in the D, L or DL form, to their salts, to their preparation and to their use.

In the general formula (I), n is an integer between 1 and 5 inclusive, m is an integer between 2 and 6 inclusive, R represents a hydrogen atom or a radical of general formula:

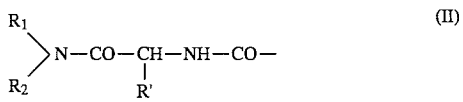

in which $R_1$ and $R_2$, which may be identical or different, each represent a saturated aliphatic radical $C_pH_{2p+2}$ or unsaturated aliphatic radical $C_pH_{2p-2}$, or p being an integer between 12 and 22 inclusive, and R' represents a hydrogen atom or an alkyl radical containing 1 to 4 carbon atoms optionally substituted with a phenyl radical, or a radical of general formula:

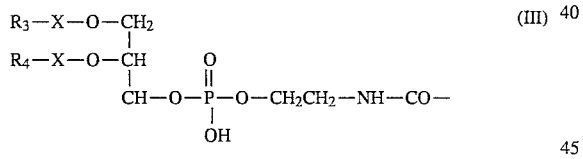

in which X represents a methylene group (—$CH_2$—) or a carbonyl group (—CO—), and $R_3$ and $R_4$, which may be identical or different, each represent a saturated aliphatic radical $C_{p'}H_{2p'+2}$ or unsaturated aliphatic radical $C_{p'}H_{2p'}$ or $C_{p'}H_{2p'-2}$, p' being an integer between 11 and 21 inclusive, on the understanding that:

irrespective of the values of m and n, only one of the symbols R represents a radical of general formula (II) or (III)

when n is between 2 and 5, the values of m in the different fragments

may be identical or different.

Of very special interest are the products of general formula (I) in which n is equal to 3 and the values of m in the fragments

are identical or different and represent 3 or 4, and R represents: either a radical of general formula (II) in which $R_1$ and $R_2$ each represent an alkyl radical containing 12 to 22 carbon atoms and R' represents a hydrogen atom, or a radical of general formula (III) in which $R_3$—X— and $R_4$—X— each represent an alkanoyl radical containing 12 to 22 carbon atoms.

Of still more special interest are 5-carboxyspermylglycinedioctadecylamide (DOGS) and dipalmitoylphosphatidylethanolamine 5-carboxyspermylamide (DPPES).

According to the invention, the new lipopolyamines of general formula (I) may be obtained by the reaction of a product of general formula:

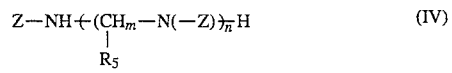

in which m and n are defined as above, $R_5$ represents a hydrogen atom or a carboxyl radical and the symbols Z represent a group protecting the amine function, on the understanding that:

irrespective of the values of m and n, only one of the symbols $R_5$ represents a carboxyl radical when n is between 2 and 5, the values of m in the different fragments

may be identical or different either with a product of general formula:

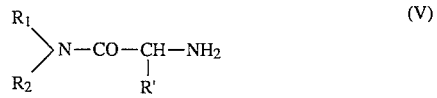

in which $R_1$, $R_2$ and R' are defined as above, or with a product of general formula:

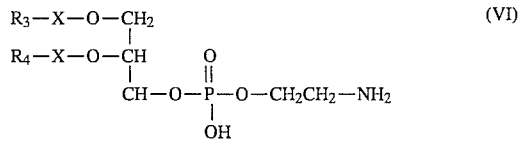

in which $R_3$, $R_4$ and X are defined as above, followed by replacement of the protective groups Z by a hydrogen atom.

When a product of general formula (V) is reacted with a product of general formula (IV), it is especially advantageous to perform the condensation in the presence of a diimide such as dicyclohexylcarbodiimide, working in an inert organic solvent selected from halogenated aliphatic solvents such as methylene chloride.

When a product of general formula (VI) is reacted with a product of general formula (IV), it is especially advantageous to treat the acid function of the product of general product (IV) beforehand with N-hydroxysuccinimide, working in an organic solvent selected from halogenated aliphatic hydrocarbons (methylene chloride) and ethers (tetrahydrofuran) in the presence of an imide such as dicyclohexyl carbodiimide, before performing the condensation of the product of general formula (VI). The condensation of the mixed ester with the product of general formula (VI) is generally performed in an organic solvent (chloroform, ethanol) in the presence of an organic base such as triethylamine at a temperature of between 30° and 50° C.

A protective group Z which is readily replaceable by a hydrogen atom without affecting the remainder of the molecule is generally used. It is especially advantageous to use as a protective group the t-butoxycarbonyl radical, which is readily replaceable by a hydrogen atom by means of an acid (trifluoroacetic acid).

The products of general formula (IV) in which n is greater than 1 may be obtained from ornithine by cyanoalkylation followed by reduction of the nitrile functions to amine functions and then protection of the mine functions thereby obtained.

The products of general formula (V) may be obtained by the reaction of an amine of general formula:

in which $R_1$ and $R_2$ are defined as above, with an amino acid of general formula:

in which R' is defined as above, in which the amine function is protected and in which the acid function is activated. It is especially advantageous to protect the amine function by a benzyloxycarbonyl radical, which is readily replaceable by a hydrogen atom by hydrogenolysis in the presence of a catalyst such as palladium. The acid function is generally activated by conversion to a p-nitrophenyl ester.

The products of general formula (VI) are known products which are readily accessible.

The new products of general formula (I) have the property, when dispersed in water, of forming unilamellar nanoparticles which are unstable in an ionic medium and which associate strongly, via their cationic portion, with plasmid or oligonucleotide DNA, compacting the latter and covering it with a lipid layer. By using an excess of cationic charges relative to the nucleic acid, the lipid/DNA complexes may be adsorbed on cell membranes, therby facilitating uptake of the DNA by the cells.

The products of general formula (I) constitute specific, non-toxic, biodegradable vectors of great efficacy for carrying out the transfection of eukaryotic cells (cell lines, primary cultures).

According to the invention, transfection is carried out by bringing a cell suspension in the absence of serum into contact with a transfecting mixture obtained, at the time of use, from a solution of the lipopolyamine of general formula (I) and a solution of the DNA in a suitable medium.

It is especially advantageous to work in a very dilute medium (1 to 5 nanomolar) and to use an excess (from 2- to 5-fold) of charges of the lipopolyamine relative to the DNA.

The transfection time can be between 10 minutes and 48 hours, independently of the nature of the cells.

The method according to the invention has the advantage of being applicable to cell lines of diverse origins (including, for example, LMKT, Ras4, CHO, F9, Bu4, S49, Hela and AtT20) as well as to primary cells, without the need to optimize or modify the conditions for carrying out the method.

Moreover, the lipopolyamines of general formula (I) enable fragile cells (intermediate or anterior hypophyseal cells, chromaffin cells, peripheral or central neurons), which it was not possible to transfect by the application of classical methods (calcium phosphate coprecipitation or dextran techniques), to be transfected.

Finally, the transfection agents according to the invention do not manifest toxicity with respect to the transfected cells. They do not manifest acute toxicity in rats after intracerebral or systemic injection.

The subject of the present invention is also a stable alcoholic or aqueous solution of a lipopolyamine of general formula (I) which is usable for carrying out cell transfections.

Solutions containing 1 mg/ml, which enable approximately 50 transfections to be carried out, are generally prepared.

The examples which follow, given without implied limitation, show how the invention may be put into practice.

EXAMPLE 1

A mixture of L-5-carboxytetra (t-butoxycarbonyl) spermine (1 equivalent) and glycinedioctadecylamide (1 equivalent) in methylene chloride is stirred for 12 hours in the presence of dicyclohexylcarbodiimide (1.1 equivalent).

After chromatography on silica, tetra(t-butoxycarbonyl)-5-carboxyspermylglycinedioctadecylamide is obtained in a 90% yield, the protective groups of which product are removed by treatment with trifluoroacetic acid for 10 minutes at a temperature in the region of 20° C. The tetrakis(trifluoroacetate) of 5-carboxyspermylglycinedioctadecylamide (DOGS) is thereby obtained.

The structure of the product obtained is confirmed by the proton nuclear magnetic resonance spectrum at 200 MHz in deuterated methanol (chemical shifts δ in ppm): 0.9 [t, $(CH_3)_2$]; 1.3 [m, $2\times(CH_2)_{15}$]; 1.4–1.7 (m, $2\times CH_2CH_2NCO$); 1.8–2.2 (m, $4\times CH_2CH_2N^+$); 3.0–3.2 (m, $5\times CH_2N^+$); 3.35 (t, $2\times CH_2NCO$); 4.0 (t, $CHN^+$); 4.15 (s, $COCH_2ND$).

L-5-Carboxytetra (t-butoxycarbonyl) spermine may be prepared in the following manner:

2.2 equivalents of acrylonitrile are added to a 1M solution of L-ornithine in dimethylformamide. The mixture is stirred for 1 hour at a temperature in the region of 20° C.

The dinitrile thereby obtained is reduced with hydrogen in the presence of Raney nickel, working in the presence of ethanolic potassium hydroxide, to give L-5-carboxyspermine, the amine functions of which are protected by t-butoxycarbonyl groups by application of the usual methods.

Glycinedioctadecylamide may be prepared by the condensation of dioctadecylamine (1 equivalent) with N-carbobenzoxyglycine p-nitrophenyl ester (1 equivalent), working in methylene chloride in the presence of triethylamine (1.1 equivalent) for 5 hours.

After hydrogenation for 1 hour in the presence of palladium on charcoal (10% palladium), working in a methylene chloride/ethanol mixture, glycinedioctadecylamide is obtained in an 87% yield.

EXAMPLE 2

L-5-Carboxytetra(t-butoxycarbonyl)spermine (1 equivalent) is treated for 12 hours with N-hydroxysuccinimide (1.1 equivalent) in the presence of dicyclohexylcarbodiimide (1.1 equivalent), working in a methylene chloride/tetrahydrofuran mixture.

The ester obtained is treated with dipalmitoylphosphatidylethanolamine (1 equivalent) in the presence of triethylamine (1 equivalent) in a chloroform/ethanol mixture for 12 hours at 40° C. After treatment of the reaction mixture, dipalmitoylphosphatidylethanolamine tetra(t-butoxycarbonyl)-5-carboxyspermylamide is obtained in a 55% yield, the protective groups of which product are removed with trifluoroacetic acid in methylene chloride. Dipalmitoylphosphatidylethanolamine 5-carboxyspermylamide (DPPES) is thereby obtained in the form of a tetrakis(trifluoroacetate).

The structure of the product obtained is confirmed by the proton nuclear magnetic resonance spectrum at 200 MHz in a deuterated chloroform/deuterated methanol mixture (1:1 by volume) (chemical shifts δ in ppm): 0.85 [t, $(CH_3)_2$]; [m, $2\times(CH_2)_{12}$]; 1.5–1.65 (m, $2\times CH_2CO_2$); 1.8–2.1 (m, $4\times CH_2CH_2N^+$); 2.3 (tt, $2\times CH_2CH_2CO_2$); 2.9–3.1 (m, $5\times CH_2N^+$); 3.2 (bm, $CH_2NDCO$); 3.75–4.05 (m, $CHN^+$, $2\times CH_2OP$); 4.15–4.40 (2×dd, $CO_2CH_2$); 5.20 (OCH).

EXAMPLE 3

A 20 mM solution of DOGS in ethanol is diluted 10-fold with sterile water so as to obtain a 2 mM solution. 7.5 μl of this solution are withdrawn and diluted in 250 μl of DMEM medium (Dulbecco Modified Essential Medium).

A solution is prepared containing 5 μg of plasmid containing a vector for the expression of chloramphenicol acetyltransferase (CAT) (for example a construction derived from plasmid pCAT 8+ [L. Klein-Hitpass et al., Cell, 46, 1053–1061 (1986)] by the insertion of a fragment (BamHI-XbaI) containing 4 copies of the AP1 sequence ["binding consensus sequence"] (pCAT 4XB)]) in 250 μl of DMEM medium.

A suspension is prepared of $10^5$–$10^6$ melanotropic cells [prepared according to B. A. Demeineix et al., Neuroscience, 17, 1275–1285 (1986)] in 500 μl of DMEM medium in the absence of serum.

The DOGS and plasmid solutions are mixed and the "transfecting" mixture is added to the cell suspension.

The mixture is incubated at 37° C. for a specified period.

After transfection, the cells are washed twice and then plated. After 48 hours, the cells are washed with phosphate buffer (PBS) and the chloramphenicol acetyltransferase activity is then determined according to the method of C. M. Gorman et al., Mol. Cell. Biol., 2, 1044–1051 (1982).

The cells are resuspended in 100 μl of a 200 mM solution of Tris-HCl (pH 7.4). After several cooling/heating cycles, 50 μl of the supernatant are added to 40 μl of Tris-HCl (pH 7.4) containing $^{14}C$-labelled chloramphenicol (0.1 μCi). After 5 minutes at 37° C., the reaction is initiated by adding 20 μl of acetyl-COA (4 mM). After 1 hour at 37° C., the chloramphenicol and its acetylated derivatives are extracted with ethyl acetate, separated by thin-layer chromatography and autoradiographed. The autoradiograms are analysed by a suitable method.

This method thus enables different promoters to be analysed in primary cultures in general.

We claim:

1. Intermediate compounds useful for producing transfecting lipopolyamines, comprising:

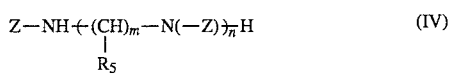  (IV)

wherein m is an integer between 2 and 6 inclusive, wherein n is an integer between 2 and 5 inclusive, wherein $R_5$ represents a hydrogen atom or a carboxyl radical but no more than one $R_5$ represents a carboxyl, the values of m in the different fragments

may be identical or different, and wherein the symbols Z represent a group protecting the amine function.

2. Intermediate compounds according to claim 1, wherein n is 3.

3. Intermediate compounds according to claim 1, wherein the compounds have the formula:

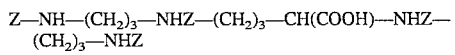

4. Intermediate compounds according to claim 1, wherein n is 3 and m is 3 or 4.

5. Intermediate compounds according to claim 1, wherein the compound is L-5-carboxytetra (t-butoxycarbonyl) spermine.

* * * * *